US006110194A

United States Patent [19]

Saber

[11] Patent Number: 6,110,194

[45] Date of Patent: Aug. 29, 2000

[54] APPARATUS FOR ALIGNING SPINAL VERTEBRAE

[76] Inventor: Kirk Saber, 865 Via De La Paz, Pacific Palisades, Calif. 90272

[21] Appl. No.: 09/006,256

[22] Filed: Jan. 13, 1998

[51] Int. Cl.[7] ........................................ A61F 5/00

[52] U.S. Cl. ........................................ 606/240; 5/633

[58] Field of Search ........................ 602/19; 606/240; 128/870; 5/633; 482/140, 142

[56] References Cited

U.S. PATENT DOCUMENTS

| | | | |
|---|---|---|---|
| 726,054 | 4/1903 | Hartford | 606/240 |
| 726,055 | 4/1903 | Hartford | 606/240 |
| 1,904,039 | 4/1933 | Bruder | 606/240 X |
| 3,601,121 | 8/1971 | Roberts | 5/633 X |
| 4,752,067 | 6/1988 | Colonello | 482/140 |
| 4,953,857 | 9/1990 | Lemire | 482/140 X |
| 5,033,742 | 7/1991 | Johnson et al. | 482/142 |
| 5,224,956 | 7/1993 | Dumas et al. | 606/240 |
| 5,279,310 | 1/1994 | Hsein | 606/240 X |
| 5,474,513 | 12/1995 | Carlesimo et al. | 482/140 |
| 5,713,841 | 2/1998 | Graham | 606/240 X |

*Primary Examiner*—Linda C. M. Dvorak
*Attorney, Agent, or Firm*—Matthew F. Jodziewicz

[57] ABSTRACT

An apparatus and method useful for urging alignment of the spinal vertebrae of a user includes using a board member having a lengthwise axis and a top surface with a channel formed therein that is generally parallel to the lengthwise axis and with sufficient length and depth to receive the spinal vertebrae of a user therein. The board member has a first and a second convex portion formed generally parallel and symmetric to and proximate the channel. A first and a second concave portion are formed in the board member generally parallel and symmetric to and distal from the channel. The convex and concave portions have sufficient curvature for applying pressure to the skeletal structure of the rib cage of a user to urge the spinal vertebrae of the user into alignment in the channel when the user lies supine on the board top surface.

34 Claims, 2 Drawing Sheets

APPARATUS FOR ALIGNING SPINAL VERTEBRAE

BACKGROUND OF THE INVENTION

This invention relates to an apparatus and method for manipulation of the skeletal structure of an individual, and more particularly, to an apparatus and method useful for aligning the spinal vertebrae of an individual.

In modem society, the individual undergoes many daily stresses impacting on general health. Even the sedentary office worker is not immune to such stress which often manifests itself in the form of muscle tension or sore backs from hours of office sitting perhaps followed by frantic attempts at physical exercise to relieve such symptoms. Many times the physical exertion only exacerbates the problem resulting in debilitating lower back pain caused by weakened or misaligned skeletal structure requiring a visit to a chiropractor or doctor to alleviate the problem by manipulation of the muscles and skeletal structure back into the proper orientation. Back pain caused by misaligned spinal vertebrae is legendary for its ability to appear at the most inopportune moments and totally disable its victim. Realignment of the spinal vertebrae can be both painful and difficult, as muscles, as well as actual bone misalignments, many times oppose realignment procedures, requiring a health practitioner to exert more force than is preferred to urge realignment.

Individuals are at an even greater disadvantage than the health practitioner as any attempt to align their own spinal vertebrae requires them to work in an area that they cannot easily reach or observe in order to apply the needed appropriate pressures. Also, if they err and a misalignment occurs, they may be incapacitated from any further action and be left helpless until aid arrives.

Consequently, a method and apparatus are desired that would aid both the practitioner and individual to align the spinal vertebrae with a minimum of difficulty, guesswork or health danger.

SUMMARY AND OBJECTIVES OF THE INVENTION

The present invention provides a solution to this problem by disclosing both a method and an apparatus useful for urging alignment of the spinal vertebrae of a user. An apparatus embodying the present invention comprises a board member having a lengthwise axis and, on its a top surface, a channel generally parallel the lengthwise axis and with sufficient length and depth to receive the spinal vertebrae of the user therein. The board member further has formed generally parallel and symmetric to and proximate the channel, a first and a second convex portion and, generally parallel and symmetric to and distal from the channel, a first and a second concave portion. Both convex and concave portions have sufficient curvature to apply pressure to the skeletal structure of the rib cage of a user to urge the spinal vertebrae of the user into alignment in the channel when the user lies supine on the board top surface.

It is an object of the present invention to provide an apparatus and method to align the spinal vertebrae of a user with a minimum of difficulty or applied force to the muscular-skeletal structure of the user.

It is another object of the present intention to provide an apparatus and method to align the spinal vertebrae of a user that permits users to do such alignment by themselves.

Other objects and novel features of construction and operation of the invention will be more clearly apparent during the course of the following description, reference being had to the accompanying drawings wherein has been illustrated a preferred form of the device of the invention and wherein like characters of reference designate like parts throughout the drawings.

BRIEF DESCRIPTION OF A PREFERRED EMBODIMENT

Figure 1:
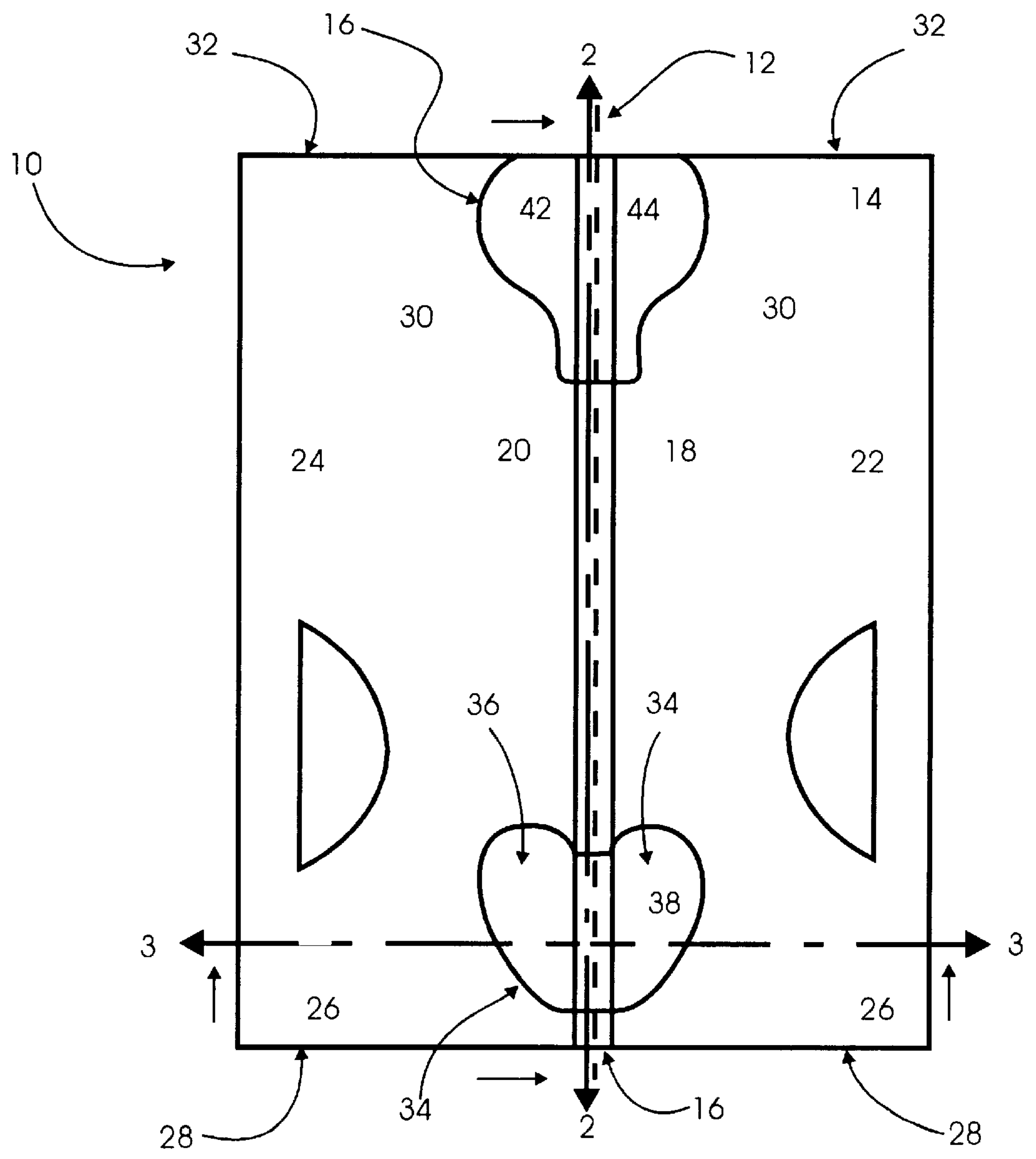
FIG. 1 is a plan view of a board member that embodies the present invention.
Figure 2:
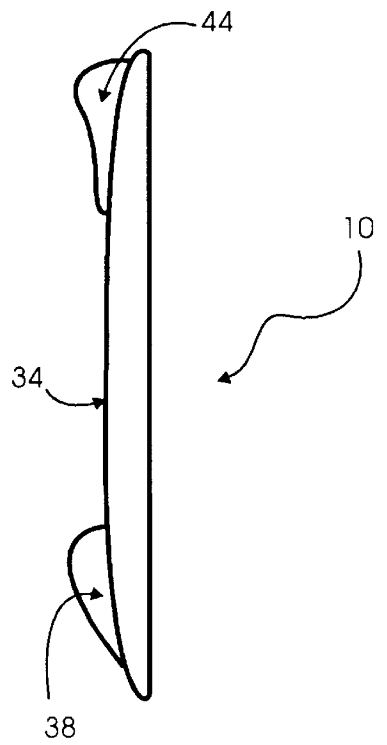
FIG. 2 is a cross-sectional view of the board member of FIG. 1 taken along line 2—2 in the direction of the arrow shown in FIG. 1.
Figure 3:
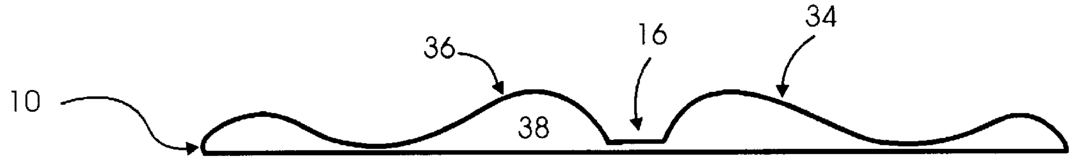
FIG. 3 is a cross-sectional view of the board member of FIG. 1 taken along line 3—3 in the direction of the arrow shown in FIG. 1.

A preferred embodiment of the present invention in an apparatus that is useful for urging alignment of the spinal vertebrae of a user that comprises a board member 10 having a lengthwise axis 12 and a top surface 14 with a channel 16 formed therein generally parallel to lengthwise axis 12 and with sufficient length and depth to receive the spinal vertebrae of a user therein. Generally, board member 10 will be rectangular in shape to accommodate the natural shape of a human back. Preferred dimensions are in the range of about 13 inches wide by about 20 inches in length. However, other shapes are not precluded from embodying the present invention and may be employed for aesthetic or manufacturing reasons.

Board member 10 has first and second convex portions 18, 20 respectively, formed generally parallel and symmetric to and proximate channel 16. Board member 10 also has formed first and second concave portions 22 and 24, respectively, generally parallel and symmetric to and distal from channel 16.

While the dimensions of channel 16 may vary to accommodate the various physical variations in the human frame, one preferred set of dimensions have been found to give channel 16 a width of about 1 inch and a depth of about ⅝ of an inch. The sides of channel 16 may also be tapered or not depending on the particulars of the skeletal structure that are to be aligned.

First and second convex portions 18 and 20, and first and second concave portions 22 and 24, have sufficient curvature for applying pressure to the skeletal structure of the rib cage of a user to urge the spinal vertebrae of the user into alignment in channel 16 when the user lies supine on board top surface 14. Preferred dimensions result in a maximum board thickness of about ¾ of an inch on the convex portions 18 and 20 and a board thickness of about ⅛ of an inch on the concave portions 22 and 24.

It is preferred that board member 10 have a first tapered portion 26 transverse to lengthwise axis 12 and proximate a first side 28 of board member 10 to facilitate use of board 10 by a user. Having tapered portion 26 will enable users to roll their back onto board member 10 without having a ridge on board member 10 jut into the user's back where it first encounters board member 10. Having tapered portion 26 also facilitates the initial entry of the user's spinal vertebrae into channel 16.

Likewise, it is preferred that board member 10 further has a second tapered portion 30 transverse to lengthwise axis 12 and proximate a second side 32 of board member 10 opposite first side 28. Second tapered portion 30 accommodates the curve of the spinal vertebrae in the neck, which curve as they approach the skull. Tapering the upper portion 30 of board member 10 allows for greater comfort on the part of the user lying supine on board member 10.

It is further preferred that board member 10 have at least one, and preferably two, handhold apertures 34 formed in it to facilitate a user in grasping or carrying board member 10.

Also, the invention includes having a lower back supporting portion 34, proximate the first side of the board 28, for providing a surface heaving curvature for supporting the lower back musculature structure of the user when the user lies supine on the board top surface 14. Such a supporting structure 34 comprises a first and second lower back supporting convex raised portion 36, 38, that are positioned generally parallel and symmetric to the vertebrae receiving channel 16. Portion 34 provides lower back lumbar supporting pressure for the user.

While the lower back supporting structure 34 may be integrally formed on the board member 10, it is preferred that lower back supporting structure 34 be removable or at least adjustable in its positioning on the board member 10 to accommodate the various anatomical differences between users. One method of adjustment would be to adapt the lower back supporting structure 10 for parallel movement along the board's lengthwise axis 12.

A complementary added embodiment includes neck supporting structure 40, proximate the second side 32 of board 10, for providing a surface having a curvature for supporting the neck vertebrae of the user when the user lies supine on the board surface 14.

Like the lower back supporting portion 34 described above, the neck supporting structure 40 preferably comprises a first and second neck supporting convex raised portion 42, 44, that are generally parallel and symmetric to the vertebrae channel 16.

While the neck supporting structure 40 may be integrally formed with board member 10, it is preferred that neck supporting structure 40 be removable or at least adjustable in its positioning on board member 10 to accommodate the various anatomical differences between users. One method of adjustment would be to adapt the neck supporting structure 40 for parallel movement along the board's lengthwise axis 12.

Lower back supporting portion 34 and neck supporting structure 40 may also be movable over the board's top surface 14 to enable pressure to be exerted for deep tissue or muscle massage in various selected areas. Additional raised portions may also be added and moved about on the board's top surface to cause the same effect of deep tissue or muscle pressure massage while the user lies on the board member 10.

Finally, the board's top surface 14, or the board 10 itself, may be made from closed cell plastics that allow for some resilience and flexibility in providing supporting and aligning pressure against the user.

The present invention is also embodied in a method for urging alignment of the spinal vertebrae of a user and comprises the steps of:

Placing the user in a supine position on a board member having a lengthwise axis and a top surface with a channel formed therein generally parallel to the lengthwise axis and with sufficient length and depth to receive the spinal vertebrae of a user therein. The board member has formed generally parallel and symmetric to and proximate the channel first and second convex portions and, generally parallel and symmetric to and distal from the channel, first and second concave portions. The first and second concave portions have sufficient curvature for applying pressure to the skeletal structure of the rib cage of a user to urge the spinal vertebrae of the user into alignment in the channel when the user lies supine on the board top surface.

Additional steps include a chiropractor, masseur or health professional using the board member described above by placing the individual whose spinal vertebrae are to be aligned on the board as previously described and applying pressure to the muscular-skeletal structure of the user to force the spinal vertebrae of the user into alignment in the board channel when the user lies supine on the board top surface.

Although specific embodiments and certain arrangements have been illustrated and described herein, it will be clear to those skilled in the art that various other modifications and embodiments may be made incorporating the spirit and scope of the underlying inventive concepts and that the same are not limited to the particular forms herein shown and described except insofar as determined by the scope of the appended claims.

I claim:

1. An apparatus useful for urging alignment of the spinal vertebrae of a user comprising:

a board member having a lengthwise axis and a top surface with a channel formed therein generally parallel to said lengthwise axis and extending generally the length of said lengthwise axis and with sufficient depth to receive the spinal vertebrae of a user therein, said board member further having formed generally parallel and symmetric to and proximate said channel a first and a second convex portion and, generally parallel and symmetric to and distal from said channel, a first and a second concave portion, said first and second convex portions and said first and second concave portions having sufficient curvature for applying pressure to the skeletal structure of the rib cage of a user to urge the spinal vertebrae of the user into alignment in said channel when the user lies supine on said board top surface; and, said board member further has a first tapered portion transverse to said lengthwise axis proximate a first side of said board member.

2. An apparatus as in claim 1 wherein said board member further has a second tapered portion transverse to said lengthwise axis proximate a second side of said board member opposite said first side.

3. An apparatus as in claim 1 wherein said board member further includes means for a user to grasp said board member.

4. An apparatus as in claim 3 wherein said means for grasping said board member comprises at least one handhold aperture formed in said board member.

5. An apparatus as in claim 3 wherein said means for grasping said board member comprises a pair of handhold apertures formed in said board member.

6. An apparatus as in claim 1 further comprising:

lower back supporting means, proximate said first side of said board, for providing a surface having curvature for supporting the lower back musculature structure of the user when the user lies supine on said top board surface.

7. An apparatus as in claim 6 wherein said lower back supporting means comprises a first and second lower back supporting convex raised portion, generally parallel and symmetric to said channel.

8. An apparatus as in claim 6 wherein said lower back supporting means is removable from said board member.

9. An apparatus as in claim 6 wherein said lower back supporting means is integral with said board member.

10. An apparatus as in claim 6 wherein said lower back supporting means is adapted for parallel movement along said lengthwise axis to adjust to the anatomical structure of the user.

11. An apparatus as in claim 1 further comprising:

neck supporting means, proximate said second side of said board, for providing a surface having a curvature for supporting the neck vertebrae of the user when the user lies supine on said board surface.

12. An apparatus as in claim 11 wherein said neck supporting means comprises a first and second neck supporting convex raised portion, generally parallel and symmetric to said channel.

13. An apparatus as in claim 11 wherein said neck supporting means is removable from said board member.

14. An apparatus as in claim 11 wherein said neck supporting means is integral with said board member.

15. An apparatus as in claim 11 wherein said neck supporting means is adapted for parallel movement along said lengthwise axis to adjust to the anatomical structure of the user.

16. An apparatus useful for urging alignment of the spinal vertebrae of a user comprising:

a board member having a lengthwise axis and a top surface with a channel formed therein generally parallel to said lengthwise axis and extending generally the length of said lengthwise axis and with sufficient depth to receive the spinal vertebrae of a user therein, said board member further having formed generally parallel to and proximate said channel a first convex portion and, distal from said channel, a first concave portion, said first convex and concave portions having sufficient curvature for applying pressure to the skeletal structure of the rib cage of a user to urge the spinal vertebrae of the user into alignment in said channel when the user lies supine on said board top surface; and, said board member having a second convex portion symmetrical with said first convex portion about said lengthwise axis.

17. An apparatus as in claim 1 further comprising said board member having a second concave portion symmetrical with said first concave portion about said lengthwise axis.

18. An apparatus as in claim 16 wherein said board member further has a first tapered portion transverse to said lengthwise axis proximate a first side of said board member.

19. An apparatus as in claim 18 wherein said board member further has a second tapered portion transverse to said lengthwise axis proximate a second side of said board member opposite said first side.

20. An apparatus as in claim 16 wherein said board member further includes means for a user to grasp said board member.

21. An apparatus as in claim 20 wherein said means for grasping said board member comprises at least one handhold aperture formed in said board member.

22. An apparatus as in claim 20 wherein said means for grasping said board member comprises a pair of handhold apertures formed in said board member.

23. An apparatus as in claim 16 further comprising:

lower back supporting means, proximate said first side of said board, for providing a surface heaving curvature for supporting the lower back musculature structure of the user when the user lies supine on said top board surface.

24. An apparatus as in claim 23 wherein said lower back supporting means comprises a first and second lower back supporting convex raised portion, generally parallel and symmetric to said channel.

25. An apparatus as in claim 23 wherein said lower back supporting means is removable from said board member.

26. An apparatus as in claim 23 wherein said lower back supporting means is integral with said board member.

27. An apparatus as in claim 23 wherein said lower back supporting means is adapted for parallel movement along said lengthwise axis to adjust to the anatomical structure of the user.

28. An apparatus as in claim 16 further comprising:

neck supporting means, proximate said second side of said board, for providing a surface having a curvature for supporting the neck vertebrae of the user when the user lies supine on said board surface.

29. An apparatus as in claim 28 wherein said neck supporting means comprises a first and second neck supporting convex raised portion, generally parallel and symmetric to said channel.

30. An apparatus as in claim 28 wherein said neck supporting means is removable from said board member.

31. An apparatus as in claim 28 wherein said neck supporting means is integral with said board member.

32. An apparatus as in claim 28 wherein said neck supporting means is adapted for parallel movement along said lengthwise axis to adjust to the anatomical structure of the user.

33. A method for urging alignment of the spinal vertebrae of a user comprising the steps of:

Placing the user in a supine position on a board member having a lengthwise axis and a top surface with a channel formed therein generally parallel to said lengthwise axis and extending generally the length of said lengthwise axis and with sufficient depth to receive the spinal vertebrae of a user therein, where said board member has formed generally parallel and symmetric to and proximate said channel a first and a second convex portion and, generally parallel and symmetric to and distal from said channel, a first and a second concave portion, said first and second concave portions having sufficient curvature for applying pressure to the skeletal structure of the rib cage of a user to urge the spinal vertebrae of the user into alignment in said channel when the user lies supine on said board top surface.

34. The method as in claim 33 further including the step of:

Applying pressure to the muscular-skeletal structure of the user to force the spinal vertebrae of the user into alignment in said channel when the user lies supine on said board top surface.

* * * * *